United States Patent [19]
Dunn et al.

[11] Patent Number: 5,928,908
[45] Date of Patent: Jul. 27, 1999

[54] METHOD FOR INTRODUCING UNIDIRECTIONAL NESTED DELETIONS

[75] Inventors: John J. Dunn, Bellport; Mark A. Quesada, Middle Island; Matthew Randesi, Upton, all of N.Y.

[73] Assignee: Brookhaven Science Associates, Upton, N.Y.

[21] Appl. No.: 08/966,958

[22] Filed: Nov. 10, 1997

[51] Int. Cl.⁶ .................................................. C12N 15/64
[52] U.S. Cl. .......................................................... 435/91.42
[58] Field of Search ................................ 435/91.1, 91.42, 435/466

[56] References Cited

U.S. PATENT DOCUMENTS

| | | | |
|---|---|---|---|
| 4,843,003 | 6/1989 | Henikoff et al. | 435/91.41 |
| 4,889,799 | 12/1989 | Henikoff et al. | 435/6 |
| 5,354,656 | 10/1994 | Sorge et al. | 435/6 |

OTHER PUBLICATIONS

Greenstein et al, The Journal of Biological Chemistry, vol. 264 (21): pp. 12627–12632, 1989.
Chang et al., *Gene* 127: 95–98 (1993).
Life Technologies, GIBCO BRL Products & Reference Guide: pp. 19–14, 19–15, and 19–32 (1997/1998).

*Primary Examiner*—Terry McKelvey
*Attorney, Agent, or Firm*—Margaret C. Bogosian

[57] ABSTRACT

Disclosed is a method for the introduction of unidirectional deletions in a cloned DNA segment. More specifically, the method comprises providing a recombinant DNA construct comprising a DNA segment of interest inserted in a cloning vector, the cloning vector having an f1 endonuclease recognition sequence adjacent to the insertion site of the DNA segment of interest. The recombinant DNA construct is then contacted with the protein pII encoded by gene II of phage f1 thereby generating a single-stranded nick. The nicked DNA is then contacted with *E. coli* Exonuclease III thereby expanding the single-stranded nick into a single-stranded gap. The single-stranded gapped DNA is then contacted with a single-strand-specific endonuclease thereby producing a linearized DNA molecule containing a double-stranded deletion corresponding in size to the single-stranded gap. The DNA treated in this manner is then incubated with DNA ligase under conditions appropriate for ligation. Also disclosed is a method for producing single-stranded DNA probes. In this embodiment, single-stranded gapped DNA, produced as described above, is contacted with a DNA polymerase in the presence of labeled nucleotides to fill in the gap. This DNA is then linearized by digestion with a restriction enzyme which cuts outside the DNA segment of interest. The product of this digestion is then denatured to produce a labeled single-stranded nucleic acid probe.

8 Claims, 1 Drawing Sheet

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 10754 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GATCCTCTTC TTCAGATGAA GAAACAAGTA AGGAAATGGA AGTGAAACCC AGTTCGGTGA        60

CTGCAGCCGC AAGTCCTGTG TACCAGGTAA CCATGAAAAC AGCTCAGTTT TAAAGGGATG       120

TGCAGGGATT GCCAGGACCT TTCAGGTAGT CCTACTTGGC ATTGCCCAAG GTTTCTGACT       180

TGAGATTCTG GATAATAGTT CTTGCCTTTC CCCATGCTAA GGGAAAGCTG TTTCTCTGGC       240

ACGTAAATAG GCATCCTGAG TCATTTTATC AAAGGTCAGC TTCACTATAC AATAACTAGG       300

ATAAATATAT TTCAGAAAAA TTGGCAAAAA GTAGAAAATT CATGATGGTA AAACATTCCT       360

GATATTTTAA AATCTCATTC AAAAGTTACC ACTTATTTTT TGTAGTATGT AACACTTTGT       420

TTTGTACCTT TGGGTTTAAC TTTCTATTCT CTCCCGTTCC ATGATTAAAG AGAAACCTCT       480

CTAAATTTAT TATATTATAA TTAATATTTT ACTCAAGCTG AAACATTGTC TCCCTTTTTG       540

CTTTACTAGT TGAAAAGTCA TATAGCTAGT GTGCCTGCAC TTACAGATCC ATTCACTGAT       600

TTACTATTTA TATCTACATA CCAAAGAACA TTTAATCGAC TTTAAAAAAT TGTTGACCAA       660

ACAGCATTCT TCAACAGGAA AGATATTTTA AAGTCATAAC AATTTAAAGA GATTTTTTGA       720

GTTGAGCCTT ATTCTGTAAA TGTACTTATT ACTAATTTTT AAAGGTTATC TATTTTTACT       780

TACTTGCTTT GATTAAATGT GAAACATACC AGGTTTGTGG TAAGGTTGAG CTGAAAATGA       840

AAATTTAGAC TAATGAGTAA GAAGCAGAAT ATTGGAGCTT TTAGTATGAT AAACTAAACT       900

TTTAAATTCA GCATACATTT ACATAATGAA CATTATTTCA GTGTAACTTA ATTTTTGGTT       960

TCTCATTTTT TTCTCAGTTG AATTATTCTT CCTAGACTTT AGGGGAAGAT TATTTCTGAA      1020

GATTATCATA ATTTAGGATT CTATGTATAT GTGTATGTAT ATGTATATGT ATATAACATG      1080

TACCTGGCTT TATGAAACTT CAAACAGTAC AAGACAGTAT AATAGTGAGA AGTCCTCTTT      1140

CTCCCCAACC ACCAGTCCCT ATGCATTTCC ACAGAGACAT TCATTACCAG GTTTTTTTTT      1200

CTTTTTTTTA GTATCCTTCC AGAGACATTC CCTATATAAA TAAGTAAACA TAGTATTTGT      1260

ACTTCAGGAT CATTTTTAAA AACCTTGCCA TAAATATTTG AGGCATTTTT TTTCTCTGTG      1320

TGATGGATTA TATATTGCAA ATTAGGTATA TTGAATTTTC TGGAATTCAT CCAAATGTGT      1380

GGCAATTTTA CCTCAGAATT TTATTTGTTG TTAAGCAAGA ATGTAAGTCT CAAATTAAAT      1440

TGATTGCTGC TAATTTTTTA CAAGCAAATT AACCTTTAAT TTTTAGGATT TCTTTTAAAA      1500

TTAAATTGCA TTTATTTTCC CTCATGTTGA AAGACTATTA GGATAACAGA AAGGTATGGA      1560

AATTGAGGTG TCTCTTACGT GCTTTTTAAG GAAAACATTT CTCCTTGGCC TAATACTCAT      1620

TAGCAAAACA TTTTATAATA GAGAAACACT ACTTGTGTGA AAGCTAGTGC AAATGGCCCA      1680
```

-continued

```
CTTTGATTTT CTTCTTTCTA GTATCTTGAA TCTGGCATTG CCACAAGCTT TAAAAAAGTT    1740

TTATCAAATA AGGACAACAA AATTTCTAGC TTGGAATTTT TGTTCTCTAC TGTTTTCTAA    1800

AAGGTATCCC AAGAGAGGGG ATAAAGAATT ATTCATATCT TAAAAAACGA AGAAATGAAG    1860

ATTGTGTCAG TTCTCCTGAA ATAGATCTGT AGATCCAATT CAGTATCAAT GAACATCTTA    1920

AAAGGTTTTT TTCTGGAAAG TGACAAATTG ATTCAAAATT TTAAAAAGG AGGATCAGTT     1980

GGAGGGCTCA CACTAATTCA AAGCTATTAT ATATTCATCA AGACAGTGTG GTAATGGTTT    2040

AAAAACATAC AAATATATTG ATGGCACAGG ATAGAGAGTC CAGAAGTAGA CCCACATACA    2100

TACAGTTAGT CTTTTTTCTC CCTTTTAACA AAAGTGCCAA AGCAATTCAA TGGGGAAAGT    2160

CTTCAAGAAC TTGTGCTGAA ACAACTGGAT GATCTGTGTA GGAAAAAAAA CGAACCTAAC    2220

TTAGCTGACA CCATACACAA AAATATTGAT TTGAGATGGA TTGTGTACCT AGACATAAAA    2280

GATAAATCTC TGACGCTTTT AGAAGAAAAC ATAGGGAAAT ATAATCTTTA TTTTGTGACA    2340

GGCAAATATT TCCTCTAGAG GGTCACAAAA AGTAACTAAT AAGGGAAAAA AATTGACAAA    2400

CTGGACTTCA TCAAAATTAA TCATCTTTTT GTTCATCAAA GAAACCATTA AGAAAATGGG    2460

CAAACCATAG ACTAGGACAA AATATTCTCA TTACATATAT CTGTAAAGGA CTTATTTCCA    2520

GAATATACTT TTTTTAAAAT CGCTCACAAA TCACTAGTAA AAGGTAAATG ATTCAATGAA    2580

AAATAATGGG CATATCCTGC TGTAATCTCA AAAAAAGGGC AGGAGGAGCA AAAGATGTGA    2640

ATAAACACTT TACAAAAGGA GTTATGTGAA TGGCCTCATT TATGATCAGA GGAATGCAGA    2700

TTAAATCCAT ATGAAACCTA GTTCTTCCAG AACTGCACAA TTTAAAAGCC TGACAGCATG    2760

AAATGTTAGC AAGGATGTGA AGCAGCTAGA TTCATAAACT TGCTAGTCAT GTAAAATAGT    2820

ACCACTACTT TGGAAAACTG GAACTTTTTA ACGTTAAATG TGTAACTCTT CTATTACTCA    2880

GCAGTTCCAC TCCTAAGTAT TAAATATTTA CCAAAAGAAA CGAAAATATG CCTATAAAGC    2940

CTTCTATTAG AATTAACTGT GCTGTTATTC ATTGCAGCAT TGTTTTGTTC GTTGTGTATC    3000

ATTGTTTTTT TAATAGTAAG AGACTGAAAA CAGCCTCAAT GTCCCATTAC TAGGAGACCA    3060

TTTAATTTAT AGTCATTGCT ATACTATCTA GCTGTAGAAA AATGAGAAGG ATCTTTATGT    3120

ATTGATATGT TTCTGAAATG TATTATTATG AAATGTAAAA AGCAGGATAC AATCCAGTAT    3180

ACATATATAT TTTTAAGTGT GTATAGATGT GGATAGAATA TCTCTAAAGG TATATTTAAA    3240

AAAATGTTTG GTGTCAGTTG CCCTTGAGAA GGGTTAAGAT AAAGAAGATA AAGGGTGAGA    3300

TAAAAAAGA GGGACTTTCC ACAGTTTACC CTTTTGTACT TTTTGAATTT TCTATCATGA     3360

ATGCAATGCT ATACACAATA TAATTTTTTT AAAAAAATCC TATACTTAGA AATGCAGATT    3420

TGAGATCAGC AAAATCAGAA ATTTAAGAAG ATGTGGCATT CTAAGCAGAG AGGTCTAAAA    3480

CTGCTGATAA GAACACTTTG AATAATGTGA ACCTGACGTG CCCACCTGAT TTATGGGATA    3540

ATCTAAAACT ATTATTCCCA AATACTAAAC TGGCTACATC AGAATCACCT GGGGAGCTTT    3600

GTCAAAATAC CTGGCCTCTA GTTCTGAGAT TTTATTATTG TTCATTAGAC CAGTGCTAGG    3660

GCATGAATGT TTTGTGTTTA TCTTTTTTTT TTCTAACTTT TATTTTAGGT TTAGGGATAC    3720

ACATGAAGGT TTGTTCCATA GGTAAACATG TGTCACAGGG ATTTGTTGTA CATATTATTT    3780

CATCACCCAG GTGTGAAGCC CAGTACTCAA TAGTTATCTT TTCTGCTCCT TTTCCTTCTC    3840

CCACCCTCCC CTCTCAAATA GACTCCAATG TCTATTGTTT CCTTCTTTGT GTTCATAAGT    3900

TCTTATCATT ACCTCCCACT TATAAGTGAG AACATGCGGT AGTTGATTTT CTGTTTCTGC    3960

ATTAGTTTGC TAAGGATAAT GGCCTCCAGC TCCAATGTTT TGTATTTAAA AGCCTCCAAG    4020

TGACTCCTGG CTTAGCCAGC TGTGGAAACC ACTGGACTAA AACAAGCATG TCCTTACAAG    4080
```

```
CTTCCATTCG TTCCATGTTT TGGTCTTTTT TGGTTGAAGT TGTTTAGGAA GTACTGTGTT      4140

TGAGTTTATT CATTTCTTTA TGCATTCAGA AAACATTGGT CACCTGTTAT ACATTATACG      4200

CCTATTACAC ATGAGGTTTT TAATGTATTT AGACCTGACA ATAGGAGTGT CACTTAGATG      4260

TGATCTCAGT GTTGTGGGTA ACTTTGTTTG TCTTTAATGA GAAATCTGGA ACATAGATGA      4320

TGATTTTTTC CTTTGAATTA ACTTAATGTG TTCTCTTCCC TACAGATTTC AGAACTTATA      4380

TTTCCACCTC TTCCAATGTG GCACCCTTTG CCCAGAAAAA AGCCAGGAAT GTATCGAGGG      4440

AATGGCCATC AGAATCACTA TCCTCCTCCT GTTCCATTTG GTTATCCAAA TCAGGGAAGA      4500

AAAAATAAAC CATATCGCCC AATTCCAGTG ACATGGGTAC CTCCTCCTGG AATGCATTGT      4560

GACCGGAATC ACTGGATTAA TCCTCACATG TTAGCACCTC ACTAACTTCG TTTTTGATTG      4620

TGTTGGTGTC ATGTTGAGAA AAAGGTAGAA TAAACCTTAC TACACATTAA AAGTTAAAAG      4680

TTCTTACTAA TAGTAGTGAA GTTAGATGGG CCAAACCATC AAACTTATTT TTATAGAAGT      4740

TATTGAGAAT AATCTTTCTT AAAAAATATA TGCACTTTAG ATATTGATAT AGTTTGAGAA      4800

ATTTTATTAA AGTTAGTCAA GTGCCTAAGT TTTTAATATT GGACTTGAGT ATTTATATAT      4860

TGTGCATCAA CTCTGTTGGA TACGAGAACA CTGTAGAAGT GGACGATTTG TTCTAGCACC      4920

TTTGAGAATT TACTTTATGG AGCGTATGTA AGTTATTTAT ATACAAGGAA ATCTATTTTA      4980

TGTCGTTGTT TAAGAGAATT GTGTGAAATC ATGTAGTTGC AAATAAAAAA TAGTTTGAGG      5040

CATGACAACG CGTGTTTCTG TTGTGTGCAT AAAAGGGGAA AGAACGGGT ATTTCCCTTC       5100

AATGTATTTA ACTAAATAGC AAAAACATTA AACAGAACGT AAGAATTTTA AAATTTCCTT      5160

TGAAAAATCA ACTATTAACC ATACTTTTCC TAAAAGACCA CATATCAGAA TATGCATATG      5220

AAAAGTTAAA AATTTGTTAG TGGTAGTTAT TGAAAATATA ATAAAACATC TTTTAACTAT      5280

CAGTGTCACT ATACATAGGG TTTTTTAACA AAGAATTTGG CTCGTACTAA TTTTGACATG      5340

ACATCTGACT TACATGTCTA ATGCCATTGC ATAAAGTAGA TGTGTTCTTA CAGCTGCTCT      5400

AATCTCTGTC CTTGTGCTTT TTTTAAAAAC ATTTAAGTCT TTACTAGAGG CCTAAAATAA      5460

AGTCAAATAA TACAATACTT CAGATTCTTC AGTAGTCCAT ATTTATACAA CTGTAATTCC      5520

ATCATCTTGT AAGGGTACTT GAACTACAAA AAGAAAAAAA GAGATATCTC TATAAGAGTT      5580

TTGATTTTTC TCCAAAGGTA AATTTTTAAA AACTAAGATC AGCAATACTT TTTCCATCAC      5640

CTTCATCTTT AAATTTGCAG TCTTAAATTA TTTGACTTAC CAGAAAAATC ACAACTTGCT      5700

AATAAATCAT TGAATGCCAT GGCTATTCCA CAAATTATTG TTATTTTTAG GAAGATAAAT      5760

TCTGTTGAAA TACAAAACTG CACAAATCAT AAAGGTATAG CTCAATAGTA TGAAAATGTC      5820

AGTTTTTAAA GTTTGCAACT TCAGAAAACT CATTTTTAAA CCTTAGAGAC TTTTCTAGCT      5880

TTAATATTGT ACTCTTTAAG CCATACACAA TTTTAACATC TCTCTAAACC ATATCTACTC      5940

TTTTCCTGAA ATCTAGTGAC TGCCTATTCA AACATGAGCA TGTTTGTTTA TTAGTGTCAA      6000

AAGGGAGATG CGTTTTATCA ATTTTTTTTA ACCAAAGTTA TTGAAAGAAA AAAAGGAAAA      6060

AAAAATTACT TTCAGAGTCA TCACACTGCT TCCTTATGGG TCCTTGAGAG TTTTGTGGTG      6120

ATAATGACAG ATTTGTAGGT GATTGGCGTA AAGTTGGAAA GTTTCAAGTA TTTTTATCAT      6180

GAAGTTAGCA GACAGAATTT ATTTATTGCT TTGCTTATGA GCAAATTGGT CCTCATCTGT      6240

AGGTTTTTCA TCTGTATTTA ACCATGTATG GAAAATACTC AAAAATTAAA AAAATACAAA      6300

TTTTAAAATA TAACTACATT GCATTAGGTA TTATCTAGAT TTAAGGATG TACATAGGTT       6360

ATATGCAAAT ACGAAGCCAT TTTATATAAG GCACTTGAGC ATCTGAGATT TTGGTATCCA      6420

GGAGGTCCTG GAACAAATCC TCCAAGGATA CTGAGGGATG ACTATATAGG TTTGTTGGGA      6480
```

```
AAATCAGAAG CATAATAGTG TAAAGAAGGA AGTGTTATTT TTGGCACATA CTTAGTAGCC    6540

AGAACATTCC ACGTTACTAC AAAATCTCCT TAATTAGTTT GACGATTAAA TGACAGGGCC    6600

TCTTGGGGAA ACCACTAGTT TTGATTCAAC TGCATACAGG TAGATGTTAT TACTCATAGA    6660

AGATTCTGCC AGTGTTTCGA CTACCCATCC TCCACCTTGT CCTGAAACTT ATTTAGAGCA    6720

AAAGAAAGCT CTCATAAATA TGGCTTTTCC AATCTATTCC TAATGAAATA AAACTGTCAC    6780

TCAGCAACTG GGTCTTAAGT TCTAGCAAGC ATGGGGTACA AAAGTTTGCC AAACCCTTTT    6840

TTAGTAGTAA TTATGACTCT AGGTGCTTTG TTCTCTTAAG TTTGTCTCCC TTAGACAACT    6900

CCAAGGTGGT CTTAAAACAT GACTACATAA TTTCAGCTTG AAAGCCTTAT CGGGCTATTT    6960

CAAGCAGGAG TGGTTTATCA CTGAACAATA ATTTGTTTAA ATTCTCCATT TTATTTTTGT    7020

ATTTGTAGGC ATAACTGCAA AGCTCTAAAT TTTATAGGTT AAACTTGGAT ATTTGAAAAA    7080

AAAAGTTTTA GTAAGTTCTA TCACATTAAT ACTAAAGCAG TGCTTATTTC TGGTTTATTA    7140

GTATAATATT TATCTCAAAG TATTTAACTT TTTAGTAAAC TTCTGTGGTT CCAAGTTAAG    7200

ATAATAAAGC ATTTATGTTG ACTTCTCACT AACAGAGGTA TGTGTTAATT TCTTATTTTA    7260

TGATTAGGAA GAGGGAAAAA TACAACACCT ACCATGTACA GTTATTGTG TAGCCATTCT     7320

GTCCATTTTA CAGATAATAG TAAATAATTT TTTTAATTTT TATTACTACA TGGCAACAAC    7380

TTATTTAATC ATCACAGCCT CAGGGGGTAT GTACCATTAT CATCCCAGTT AGATAAGGAT    7440

TCCAGAGAAG TTAAAAATGC CCAAGATCAC AGAAAACTAA ATAATGAAGC TCTGACTTAA    7500

AACCCAGCTG GGCTTTTTTA AGGCCCATGC CATGGTACCT TGCCATCAGA TTCATTTTGT    7560

TACCTATAAA ATCTACCAAA TCTTGAAACT TGTAAGAAGG TTCATTATCA GACCAAGATT    7620

TTTTTAAAAA AAGGAACCAT GCGAAGGTAA ATTAATGAGA ATATAAGACA TTAAAGTATC    7680

TATTGATTAA CCACTAATAA ATCTTTGGCC AAGTTTCTTG TTACAAACTA CTCAATATAT    7740

CTGAAGAGGG AGCTGGCTGA TCATCTGATA GTAATTTTAT TGCTGGAAAT AGAAATTAAA    7800

TTGCAATAAA CAGTACAACC CAGTAGAGTG AAGACTGAGA TGACAAAGCA AACTGTACCA    7860

ATGACTTGTT ACATGGAAAG ATCACACATA ATGAGTAGTA ATTCCCAAGT CTGTCACAGT    7920

CTTTAACTTT TTTTTCTTAC TTATCAGTTA CTTGGCAATT TAACAGAGTG TACAACGTTA    7980

GTAAACTTTG TGCCAAATTT CTTCATATAC TCTGGAATCT ATTGCAATGG ATGAAGCAAT    8040

AACATTGTGA GGCTCTTACG GAAACACAAC AATATCCCTG CATTGCATAT GGCACTTTAT    8100

GGCATTGACT CGTACTGCGA AGTTGTCACA CAAGCACTCA TGAGCACAAG GGAAGGCTCA    8160

TGCAATTCCT CTTTAAAATA TGTACATTTT ATTCATTGCA GAAACCATCA CCCACTTCCA    8220

AATTTAATAG CATTAGTCCA TCTTCTATGT TCCTTTGTTC TTTCATGTAT ACTTTTAAGG    8280

GTAACATAAG GACAAAGTG GAAGCATGTT TAACCCTTAT CAAAAACAAA TTCACCATTA     8340

AGACTTGTAG CAGATACATC ACTGCAATTA GGGTAGTTTG ATGTTTATTC TGTAAAGCAC    8400

ACAATCAGCA CAAATAAAAG TACTGAATTT GTTTCTCCTA TCAAAAAAAA AAAAAATACC    8460

TAGCTACAAA AATTTCTTCC ATAAAAGTTA AGAAACATAA TCATGGGAGA CTTTGTGTTT    8520

AAATTTCATA GGACTTAAAA ATACTAATTA TGATTTAGAC AGCAATGCCA TGGCTAAAAA    8580

ATGTTTATTT GTGTGTATAC ATATATAAAA TTTATAAAAT ATAAATCCAT AGGGAATATG    8640

GGTGAAACAC ATTTCTATCT AGACTAGAGG TTTAATGGAT CATTTCTGTG TATAATATTA    8700

GTGTTATGAC CAATAAATAT ATGAACACTA AATACAAATT AAAACATTTA TTTTGGGAAT    8760

CAAAATTAAT AATGCCCAAT ATTGGTGAGG GTGTAGGGGA AGCAGTCTCT TACAGTGTTA    8820

CTAGAGGCTT AAAGAGGAGG GCAGTTACAC CTTCTTGAAG TATATATCCC TTGATCAAGC    8880
```

```
AATTGTACGT ACTTCTAGAA ATTTATCTAC AGAAGTACTC AAACGAGGAC CATTACCTAC    8940

GTAATAAGTG TTCACTGCAA AATTGTTTTG GGTGGCAAAA ATAACAAAAG CCCAAGTAGC    9000

CACCAATAGA TGAACAGTTT AATAAAATTT GAACATCTGT TCAAGGAAAT GCTGTGGAAA    9060

ATACCATGTA GCCATTAAAA AAGAGTAGAA TAAAAAAAAA AATGGTATGC CTAGAATGGT    9120

GCTAGTATTG TCTGGGGGCA AAAAATTGTT AATGGTAGTT AGTGTTCTCA AGGCGGGGAA    9180

TGGGACAAAT ACAGAGAATA TTATTTTTCT ACTTTCAACA TTTTGATCTT TAAATTTTTA    9240

TATTGAGCAT TATTACTTTG TAACTGGAGG GTAAAAAGAC ACTTTCTCAA AGGGCTTTAA    9300

GACAAGTTCA ATGGATTTAT TTTTAGCAGA TGCAAATGCT GCCATCAGTG ATAATCAAAT    9360

TGTATGTTTT GTGGACAATC TGTTGTATTT CTGAATTAAA CAATTGCAAT GTGGCTACAG    9420

TTTTATGTTT GTAATCATAC TGTGTCTACA AGGAAATATT CTGAAATAGT AAATACTTAT    9480

AATGGGGTAG CAATAGTGCA TAGTTTCCTC CAGTGTTCCC ATTATATATA ATATGATAAT    9540

ATTCATGAGA AAAATGTTAA ATATAGTATT TGGTGGGAGA AAACCCCATT ATTAAGAAAA    9600

AGTATTTAGG GAGTAGAGGG ATGCAAAAAA GAAAAGTGAA AGAAAATTTA TTAAATACCT    9660

TGGAAATAAA CTTTAACAAC AACAAAAAAG GAGTGAGTCC TATAGAGAAG AAAATTATTA    9720

AAATTTGGTG AAAGACAAAA CTGAATAGAA GAATATATCA TTTTTAAATG GACCTGATAT    9780

TATAAAAGCT TTACTTTTCT ACAAATTAAT ACATAAAGTC AATAGAAATC ATAATTTTAA    9840

AATCCCAGCA AAATTTTATG TAACTAGAAA GCCTGATTTT AAGTTTACAT GGAAGAGTAA    9900

ATTTCAAGAA TTACCAAGAA TTGTTTTAAG TAAAACAATG AGCAGAGAGT ATTTTTCCTT    9960

TTACATTATT TATTAATACA TACTTGAAGT ATAACATAGG AATAAACTAA TTCACCAGTG    10020

AAACAGAATT ACAGATCCAG AACCGAAACA TTTATATACA GAAGTTTGGT GAATGGGGCT    10080

TTTCAAATTA AAGATGAAGA ATCCACTAAT CAAAAATTAA TAGGTATTCT TATACACCAA    10140

TAACAGACAA ACAGAGAGCC AAATCATGAG TGAACTCCCA TTCACAATTG CTTCAAAGAG    10200

AATAAAATAC CTACGAATCC AACCTACAAG GGATGTGAAG GACCTCTTCA AGGAGAACTA    10260

CAAACCACTG CTCAATGAAA TAAAAGAGGA TACAAACAAA CGGAAGAACA TTCCATGCTC    10320

ATGGGTAGGA AGAATCAATA TCGTGAAAAT GGCCATACTG CCCAAGGCAA TTTATAGATT    10380

CAATGCCATC CCCATCAAGC TACCAATGAC TTTCTTCACA GAATTGGAAA AAACTACTTT    10440

AAAGTTCATA TGGAACCAAA AAAGAGCCCG CATTGCCAAC TCAATCCTAA GCCAAAAGAA    10500

CAAAGCTGGA GGCATCACAC TACCTGACTT CAAACTACAC TACAAGCCTA CAGTAACCAA    10560

AACAGCATGG TATTGGTGCC AAAACAGAGA TATAAACCAA TCGAACAGAA CAGAGCCCTC    10620

AGAAATAACG CCACATATCT ACAACTATCT GATCTTTGAC AAACCTGAGA AAACAAGCA     10680

ATGGGGAAAG GATTCCCTAT TTAATAAATG GTGCTGGGAA AACTGGCTAG CCATATATAG    10740

AAAGCTGAAA CTGG                                                      10754
```

METHOD FOR INTRODUCING UNIDIRECTIONAL NESTED DELETIONS

This invention was made with Government support under contract number DE-AC02-76CH00016, awarded by the U.S. Department of Energy. The Government has certain rights in the invention.

BACKGROUND OF THE INVENTION

DNA sequencing is a fundamental research tool with wide-ranging applications. A common approach to DNA sequencing involves the subcloning of a large DNA fragments as smaller, overlapping fragments, the sequences of which are subsequently determined using the dideoxynucleotide chain termination approach (Sanger and Coulson, *Proc. Natl. Acad. Sci. USA* 74: 5463 (1977)).

Subcloning, and the restriction mapping required to efficiently subclone fragments, is a time consuming and labor intensive process. However, given the limitations associated with the amount of sequence which can be determined from a single extension reaction, it is necessary to initiate new sequencing reactions at a distance of about every 300–400 base pairs along a fragment, the sequence of which is to be determined.

One alternative to the subcloning approach is described by Henikoff et al. in U.S. Pat. Nos. 4,843,003 and 4,889,799. More specifically, Henikoff et al. describe a method in which a vector containing a DNA sequence of interest is linearized by digestion at two restriction endonuclease recognition sites, one generating a 5' overhang and the other a blunt end or 3' overhang. Timed digestion with *E. coli* Exo III from the 5' overhang, followed by treatment with a single-strand-specific nuclease generates a nested array of deletions. Unfortunately, this technique also is limited by the need for conveniently located restriction endonuclease recognition sequences.

An alternative to the approach described above was outlined by Chang et al. (*Gene* 127: 95 (1993)). Chang et al. describe a method in which a single-stranded nick is introduced at a position adjacent to the site at which a DNA fragment having a sequence which is to be determined is inserted in a cloning vector. The nick in the DNA is then extended under controlled digestion conditions to produce a single-stranded gap. The single-stranded gap is then treated with a nuclease which specifically digests single-stranded DNA, thereby producing a deletion within the DNA sequence of interest.

Chang et al. specifically report that the single-stranded nick in the DNA of interest cannot be expanded by treatment with *E. coli* Exo III. Given the fact that Exo III is a well-understood, relatively inexpensive enzyme, Chang et al. note that this is an unfortunate finding (page 96, column 2). The development of protocols which would enable the use of Exo III in such a DNA sequencing strategy would represent an important improvement in the art.

SUMMARY OF THE INVENTION

The present invention relates, in one embodiment, to a method for the introduction of unidirectional deletions in a cloned DNA segment. More specifically, the method comprises providing a recombinant DNA construct comprising a DNA segment of interest inserted in a cloning vector, the cloning vector having an f1 endonuclease recognition sequence adjacent to the insertion site of the DNA segment of interest. The recombinant DNA construct is then contacted with the protein pII encoded by gene II of phage f1 thereby generating a single-stranded nick. The nicked DNA is then contacted with *E. coli* Exonuclease III thereby expanding the single-stranded nick into a single-stranded gap. The single-stranded gapped DNA is then contacted with a single-strand-specific endonuclease thereby producing a linearized DNA molecule containing a double-stranded deletion corresponding in size to the single-stranded gap. The DNA treated in this manner is then incubated with DNA ligase under conditions appropriate for ligation.

In another embodiment, the invention relates to methods for producing single-stranded DNA probes. In this embodiment, single-stranded gapped DNA, produced as described above, is contacted with a DNA polymerase in the presence of labeled nucleotides to fill in the gap. This DNA is then linearized by digestion with a restriction enzyme which cuts outside the DNA segment of interest. The product of this digestion is then denatured to produce a labeled single-stranded nucleic acid probe.

DETAILED DESCRIPTION OF THE INVENTION

Figure 1:
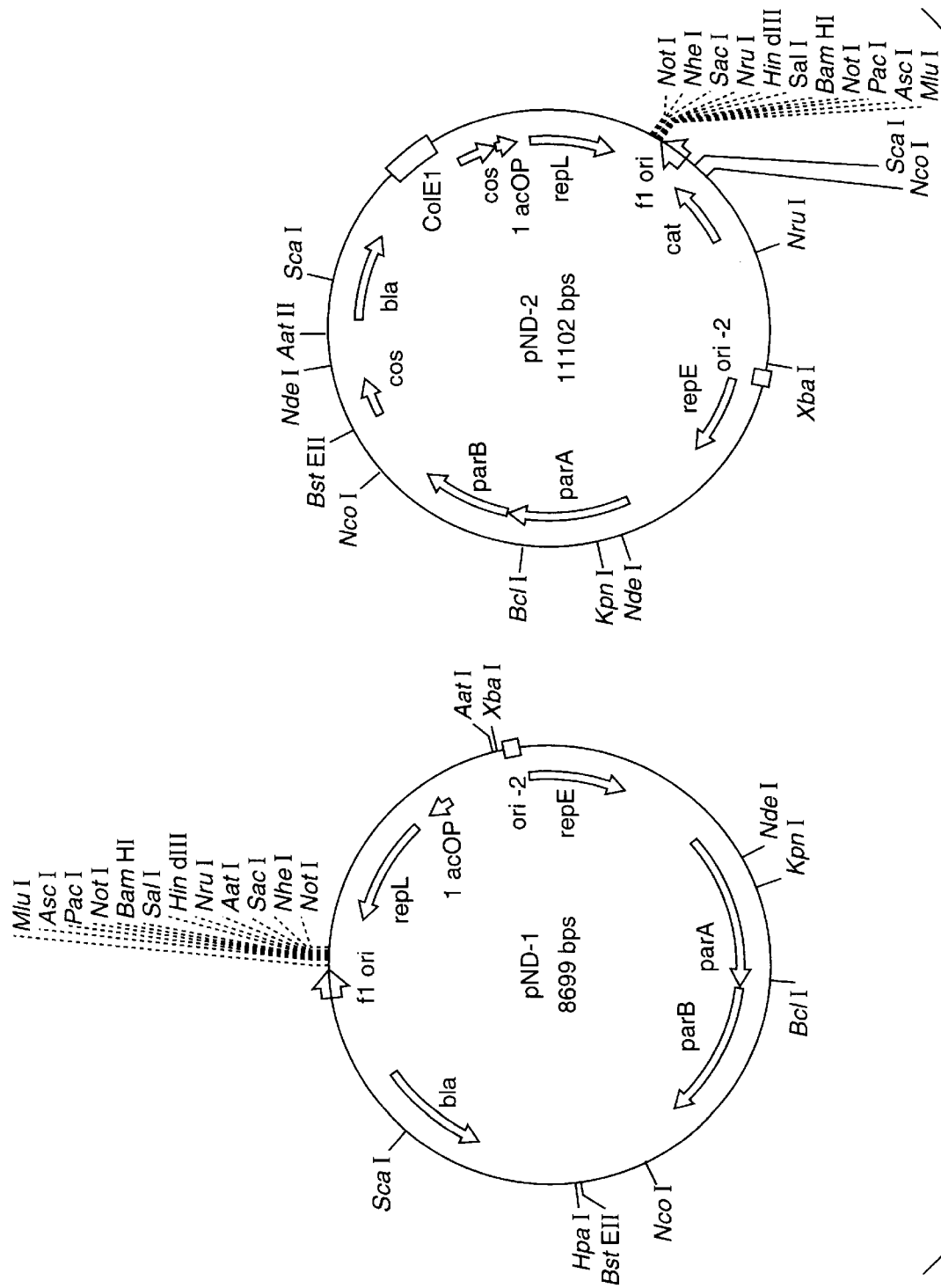
FIG. 1 is a diagrammatic representation of the vectors pND-1 and pND-2.

The subject invention relates to a universal method for generating a nested set of unidirectional deletions within a cloned DNA fragment. The method is applicable to a variety of molecular biological applications including, for example, DNA sequencing and the production of labeled single-stranded probe sequences. The method is based on the surprising discovery that *E. coli* Exo III is capable of extending a single-stranded nick, introduced into double-stranded DNA by the phage f1, gene II product, into a gapped structure.

As discussed in the background section, the prior art teaches that *E. coli* Exo III is incapable of extending a nick in double-stranded DNA, introduced into double-stranded DNA by the phage f1, gene II product, into a gapped structure. As shown in the experiments described below, this teaching is incorrect.

More specifically, Applicants produced a recombinant DNA construct comprising a DNA segment of interest inserted in a cloning vector, the cloning vector having an f1 endonuclease recognition sequence adjacent the insertion site of the DNA segment of interest. The recombinant DNA construct was contacted with the protein pII encoded by gene II of phage f1 thereby generating a single-stranded nick. This digestion was carried out in the presence of the divalent cation $Mn^{2+}$. The nicked DNA was then treated with *E. coli* Exo III thereby expanding the single-stranded nick into a single-stranded gapped structure. The Exo III digestions were carried out under timed conditions to generate molecules having singled-stranded gaps of varying sizes.

The single-stranded gapped DNA is then treated with a single-strand-specific endonuclease (e.g., mung bean or S1 endonuclease) thereby producing a linearized DNA molecule containing a double-stranded deletion corresponding in size to the single-stranded gap. The DNA containing the double stranded deletion is then incubated with DNA ligase under conditions appropriate for ligation. In a preferred embodiment of the present invention, dNTPs and DNA polymerase are included in the ligation reaction to blunt any ragged ends which may have been produced in the deletion process.

When used in connection with DNA sequencing protocols, this method of producing unidirectional nested deletions can be fine-tuned to result in an ordered set of nested deletions whose ends are separated by about 300–400 base pairs. This allows rapid sequencing across one strand of a cloned DNA fragment using a universal primer. Any gaps remaining after this process can be closed by primer walking on the original clone. Even highly repeated DNA can easily be assembled correctly, knowing the relative locations of the sequences obtained. As shown in the Exemplification section which follows, the disclosed method has been employed to determine the DNA sequence of cloned fragments at least as large as 17 kb. It is reasonable to postulate an upper limit of 40–50 kb for the size of cloned fragments which can be sequenced in this manner.

Two specific vectors (pND-1 and pND-2) were used in connection with the experiments described below. Both are single-copy amplifiable vectors stably maintained at low copy number by the F replication and partitioning functions and can be amplified from an IPTG-inducible P1 lytic replicon to prepare DNA. A synthetic version of the phage f1 origin of replication is located a short distance upstream of the multiple cloning site. Vector pND-1 was used primarily for obtaining clones by transformation or electroporation. Vector pND-2 has phage lambda cos sites that allow efficient cloning of 30–40 kbp fragments in a lambda packaging system.

Although the demonstration below was accomplished with the two low copy number vectors, one of skill in the art will recognize that the teachings of the present invention apply to any type of cloning vector.

Reaction conditions have been defined where purified f1 gene 2 protein efficiently introduces a strand-specific single nick in the f1 origin sequence with very little rejoining. Large amounts of stable gene 2 protein are obtained using recombinant DNA production techniques. The Exo III digestion is highly synchronous and processive, and the deletion lengths are proportional to incubation time. In one embodiment, to prevent undeleted DNA from giving rise to clones, treated DNA is digested with one of several restriction enzymes whose 8-base recognition sequences lie between the f1 origin and the cloning site. Nested deletion clones are then obtained by electroporation.

Pooling samples from several different times of Exo III digestion before subsequent treatment generates a good distribution of deletion clones. Growth and amplification of randomly selected clones in 1 ml of medium in 96-well format followed by a simple DNA preparation protocol provides ample DNA for analyzing deletion length by gel electrophoresis and for DNA sequencing reactions. Imaging and sizing software is now being tested for automated selection of an appropriate set of deletions for sequencing.

In addition to the method for producing nested deletions discussed above, the invention also relates to a method for producing labeled single-stranded DNA probes. The method for producing labeled single-stranded DNA probes is essentially identical to the method described above for producing nested deletions, through the DNA gapping step. However, rather than digesting single-stranded DNA with an endonuclease following the gapping step, the gap is instead filled in by a DNA polymerase in the presence of labeled dNTPs. The molecule is then linearizing by digestion with a restriction enzyme which cuts outside the DNA segment of interest. The product is then denatured (e.g., by heating) to produce a labeled single-stranded nucleic acid probe.

EXEMPLIFICATION

Materials

The following reaction buffers were prepared:

| | |
|---|---|
| i) | 10x GeneII buffer |
| | 200 mM Tris pH 8.0 |
| | 800 mM KCl |
| | 50 mM DTT |
| ii) | 1x ExoIII Buffer(USB) |
| | 66 mM TrisCl pH 8.0 |
| | 6.6 mM MgCl$_2$ |
| | 5 mM DTT |
| | 50 µg/ml BSA |
| iii) | S1 Stop Mix |
| | 0.3M TrisCl |
| | 50 mM EDTA |
| iv) | 2x Fill-in & Ligation Mix |
| | 40 mM Tris pH 7.6 |
| | 20 mM MgCl$_2$ |
| | 20 mM DTT |
| | 1.2 mM ATP |
| | 200 µM of each dNTP |

Methods

Double-stranded DNA was nicked by combining the following reagents:

2 µg DNA(for inserts>20 kb: 4 µg DNA)

4 µl 10x Gene II Buffer

2 µl 50 mM MnCl$_2$

20 µl GeneII serially diluted ⅛

The total reaction volume was brought to 40 µl with the addition of sterile water and the mixture was incubated at 37° C. for 1 hour. The nicked DNA was then phenol extracted and ethanol precipitated. The nicked DNA was then resuspended in 50 µl 1x Exo III Buffer (USB).

2 µl Exo III (200 U, USB) was added to a prewarmed tube containing phenol extracted, nicked DNA. The mixture was incubated at 37° C. 2.5 µl aliquots were sampled at 30 second intervals and mixed with 2.5 µl of S1 nuclease mix (0.5 µl S1 nuclease buffer, 1.25 U S1 nuclease, brought to 2.5 µl with distilled water) on ice. After last time point, all tubes were transferred to 30° C. for 30 minutes. 1 µl of S1 nuclease stop mix was added and the tubes were heated at 70° C. for 10 minutes. 2 µl of each time point was checked by gel electrophoresis. All time points were then combined and ethanol precipitated. The DNA was resuspended in 25 µl Tes1.

To recircularize the deletion-containing DNAs, 25 µl 2x fill-in and ligation mix was added to the above, together with 1 µl T4 DNA ligase (6 Weiss units) and 0.5 µl (2 units) T4 DNA polymerase. The mixture was sonicated at 14 degree C for 10 minutes and incubated at 14° C. overnight. The enzymes were heat-inactivated at 68° C. for 15 minutes, followed by digestion with a restriction enzyme having an uncommon recognition sequence (e.g., PacI or AscI). Following digestion, the DNA was phenol extracted, ethanol precipitated and resuspended in 10 µl sterile water. Cells were then transformed by electroporation with 5 µl DNA and plated on selected antibiotics.

Results

A partial sequence of the human adenovirus receptor gene was determined in the manner described above. A BAC clone containing the human adenovirus receptor gene was purchased from Research Genetics (Huntsville, Ala.). The human DNA insert in this BAC clone is approximately 110 kilobases in length. The BAC DNA was isolated for subcloning by standard techniques. The DNA was digested with the restriction enzyme Bam H1 which yielded approximately 16 fragments. These fragments were individually subcloned into the pND2 vector. All subclones were sequenced in both directions. Nested deletions were performed on 5 of these fragments. In particular, a 10 kb fragment was sequenced completely by the nested deletion strategy. The sequence determined is shown in SEQ ID NO: 1.

We claim:

1. A method for introducing unidirectional deletions in a cloned DNA sequence, the method comprising:
 a) contacting a recombinant DNA construct comprising a DNA sequence of interest inserted in a cloning vector, the cloning vector having an f1 endonuclease recognition sequence adjacent to an insertion site of the DNA sequence of interest, with protein pII encoded by gene II of phage f1 thereby generating a recombinant DNA construct with a single-stranded nick;
 b) digesting the recombinant DNA construct with a single-stranded nick of step a) with E. coli Exonuclease III thereby expanding the single-stranded nick into a single-stranded gap, thereby generating a recombinant DNA construct with a single-stranded gap;
 c) contacting the recombinant DNA construct with a single-stranded gap of step c) with a single-strand-specific endonuclease thereby producing a linearized DNA molecule containing a double-stranded deletion corresponding in size to the single-stranded gap of step b); and
 d) ligating the linearized DNA molecule of step c) containing the double-stranded deletion with DNA ligase.

2. The method of claim 1 wherein the cloning vector is a single copy cloning vector.

3. The method of claim 1 wherein the cloning vector is a high copy cloning vector.

4. The method of claim 1 wherein the single-strand-specific endonuclease is S1 nuclease.

5. The method of claim 1 wherein step b) is timed to produce a single-stranded gap having a specific length, the time of digestion required for said specific length being determined by empirical experimentation.

6. The method of claim 1 wherein step a) is carried out in a buffer containing the divalent cation $Mn^{2+}$.

7. The method of claim 1 wherein the cloning vector further comprises a sequencing primer binding site.

8. The method of claim 1 wherein the the single-strand-specific endonuclease is selected from the group consisting of S1 endonuclease and mung bean endonuclease.

* * * * *